(12) United States Patent
Borzeix Concaix

(10) Patent No.: US 6,596,265 B1
(45) Date of Patent: Jul. 22, 2003

(54) USE OF SOPHOROLIPIDS COMPRISING DIACETYL LACTONES AS AGENT FOR STIMULATING SKIN FIBROBLAST METABOLISM

(75) Inventor: Frédérique Borzeix Concaix, Rueil-Malmaison (FR)

(73) Assignees: Institut Français du Pétrole, Rueil-Malmaison Cédex (FR); Sophor S.A., Rueil-Malmaison (FR)

( * ) Notice: Subject to any disclaimer, the term of this patent is extended or adjusted under 35 U.S.C. 154(b) by 0 days.

(21) Appl. No.: 09/701,414

(22) PCT Filed: May 27, 1999

(86) PCT No.: PCT/FR99/01245
§ 371 (c)(1),
(2), (4) Date: Nov. 29, 2000

(87) PCT Pub. No.: WO99/62479
PCT Pub. Date: Dec. 9, 1999

(30) Foreign Application Priority Data

May 29, 1998 (FR) .............................................. 98 06789

(51) Int. Cl.⁷ ............................. A61K 7/06; A61K 6/00; A61K 7/00
(52) U.S. Cl. ...................... 424/70.1; 424/401; 424/70.1
(58) Field of Search .................................. 424/701, 401; 514/880, 881, 937, 938, 944

(56) References Cited

U.S. PATENT DOCUMENTS 5,756,471 A * 5/1998 Hillion et al. ................. 514/25
6,057,302 A * 5/2000 Borzeix ....................... 514/54

FOREIGN PATENT DOCUMENTS

| EP | 209783 | | 1/1987 |
|---|---|---|---|
| EP | 0 209 783 | * | 1/1987 |
| EP | 850641 | | 7/1998 |
| FR | 2735979 | | 1/1997 |
| FR | 2740779 | | 5/1997 |
| WO | 9534282 | | 12/1995 |

* cited by examiner

Primary Examiner—Thurman K. Page
Assistant Examiner—Todd D Ware
(74) Attorney, Agent, or Firm—Millen, White, Zelano & Branigan, P.C.

(57) ABSTRACT

The invention concerns the use of sophorolipids in lactone form comprising a major part of diacetyl lactones as agent for stimulating skin dermal fibroblast cell metabolism and more particularly as agent for stimulating collagen neosynthesis, at a concentration of 0.01 ppm at 5% (p/p) of dry matter in formulation. The invention is applicable in cosmetology and dermatology.

12 Claims, No Drawings

USE OF SOPHOROLIPIDS COMPRISING DIACETYL LACTONES AS AGENT FOR STIMULATING SKIN FIBROBLAST METABOLISM

The invention relates to the use of at least one sophorolipid in the lactone form, as an agent for stimulating the metabolism of skin dermis fibroblast cells.

The invention is of particular application to the fields of cosmetology and dermatology.

Sophorolipids are glycolipids; they are produced by fermentation using Candida or Torulopsis type yeasts such as *Torulopsis magnoliae, Candida bombicola, Candida apicola* or *Candida bogoriensis*.

The constituent glucide in extracellular sophorolipids is sophorose (2-O-β-D-glucopyranosyl-β-D-glucopyranose). That sugar can be acetylated in the 6' and 6" position and is bonded to a fatty hydroxyacid in the ω or ω−1 position via an acetal bond.

The lipid fraction of sophorolipids is composed of a plurality of fatty hydroxyacids which differ in their chain length, in the number and position of the unsaturated bonds, and in the hydroxylation position. For each of these hydroxyacids, there are different structural forms which differ from each other by a lactonisation (or not) of sophorose (principally in the 4" position) or by an acetylation (or not) in the 6' or 6" positions.

The mixtures of lipid sophoroses produced by fermentation can be resolved and analysed by high performance liquid chromatography using a water-acetonitrile elution gradient. About twenty individual compounds have been observed.

In their unrefined form, sophorolipids are constituted by a mixture of at least one sophorolipid in the lactone form and at least one sophorolipid in the acid form.

The respective contributions of each of the constituent hydroxyacids determined by gas chromatography for the different classes of sophorolipids and the distribution of these classes are shown below. The most abundant fatty hydroxyacid constituent, for example, is 17-hydroxyoctadecenoic acid (17-hydroxyoleic acid).

| Types  | Fatty hydroxyacids    | %    |
|--------|----------------------|------|
| C 16:0 | 15-OH hexadecanoic   | 1.5  |
| C 16:0 | 16-OH hexadecanoic   | 2.0  |
| C 18:0 | 17-OH octadecanoic   | 3.5  |
| C 18:1 | 17-OH octadecenoic   | 60.0 |
| C 18:1 | 18-OH octadecenoic   | 12.0 |
| C 18:2 | 17-OH octadecadienoic| 7.0  |
| C 18:2 | 18-OH octadecadienoic| 14.0 |

The properties of the unrefined sophorolipids and sophorolipids in the acid form which are relevant to countering cutaneous ageing, namely their action as an anti-radical and anti-elastase protective agent and their repairing, restructuring and firming action, have been described in International patent application WO 95/34282 and French patent application FR 96/16093 respectively.

Further, prior art is illustrated in European patent EP-A-0 209 783, FR-A-2 735 979 and EP-A-0 850 the latter of which describes the use of sophorolipids in the unrefined or acid form as an agent for stimulating the metabolism of dermal fibroblasts.

Properties pertaining to stimulation of the metabolism of skin fibroblasts by the lactone fraction of the sophorolipids, isolated and purified from the mixture obtained from fermentation, have not been described. This constitutes the subject matter of the invention.

The mechanical properties of the skin are primarily due to collagen fibres which constitute the principal framework of the dermal matrix.

Collagens are constituted by a family of about twenty distinct proteins, half of which are represented in the dermis. They are proteins which are rich in proline and hydroxyproline and are synthesised by fibroblasts.

On ageing, the metabolism and/or structure of the collagens can be modified. A reduction in collagen synthesis and an increase in fibre cross-linking is observed. Further, during cutaneous ageing, cell renewal is slowed down.

Unrefined sophorolipids obtained by fermentation using the process described in EP-B-0 516 803 have a beneficial action on the synthesis of collagens by dermal fibroblasts, as described in the Applicant's patent application FR 96/16093.

The lactone fraction of sophorolipids has been isolated and purified from a sophorolipid mixture obtained after fermentation.

Purification is carried out by precipitation and crystallisation from ethanol using a protocol described, inter alia, by A. P. Tulloch et al., (Can. J. Chem. 40, 1326 (1962)).

At the end of the purification process, the lactone fraction obtained is a white solid. Thin layer chromatographic analysis shows that the product is generally composed of 95% of sophorolipids in the lactone form, the majority of which are in the diacetylated lactone form.

It has been shown that this lactone fraction of the sophorolipids comprising diacetylated lactones as the major portion could be effectively used as an agent for stimulating the metabolism of skin dermis fibroblast cells.

The lactone fraction can preferably comprise at least 70% by weight of diacetylated lactones, more particularly at least 80% by weight. It is obtained by dissolving the unrefined sophorolipids in ethanol, crystallising then filtering and re-crystallising from ethanol followed by filtering. The recovered product is washed then dried.

A lactone fraction comprising a mixture of sophorolipid lactones with the formula given below is preferably used, in which formula R is an acetyl group, and where $R_1$ is a hydrogen atom or an alkyl group containing 1 to 9 carbon atoms when $R_2$ represents a chain containing 7 to 16 carbon atoms, or $R_1$ is hydrogen or a methyl group when $R_2$ represents a saturated or unsaturated hydrocarbon chain containing 12 to 17 carbon atoms.

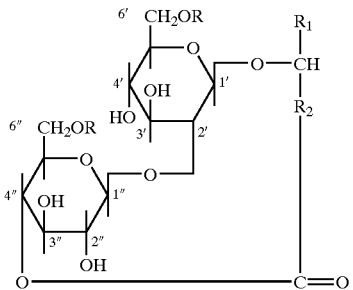

The purified sophorolipid fraction in the mainly diacetylated lactone form is active as a re-structuring, agent and connective tissue repairing agent and thus acts against cutaneous ageing. More precisely, it stimulates collagen neosynthesis in vitro, advantageously more than the unrefined sophorolipid mixture obtained on fermentation.

The purified sophorolipid fraction can be used in concentration ranges or 0.01 ppm to 5% (w/w) of dry matter in the formulation and in particular in water/oil emulsions, oil/water emulsions, gels, serums, lotions or shampoos.

More particularly, it is used in concentration ranges of 50 ppm to 1% (w/w) of dry matter.

The purified lactone fraction can be used alone in the formulation or it can be associated with the unrefined sophorolipid mixture obtained after fermentation where the pH is in the range 3 to 7.5, or it can be associated with deacetylated acid sophorolipids prepared in accordance with FR 96/16093, protonated and/or in the acid form, at least partially in the form of monovalent or divalent metal salts.

The deacetylated acid sophorolipids can also be used in a derivative form, for example in the form of an ester. In this case, their fatty acid function is at least partially esterified by reaction with a linear or branched alcohol containing 1 to 18 carbon atoms, preferably 1 to 8 carbon atoms. The esters can also be associated with the purified sophorolipid fraction described in the present application.

When associated with the purified lactone fraction of the invention, the unrefined sophorolipids can be used in a concentration of 0.01 ppm to 10% (w/w) of dry matter, more particularly 80 ppm to 2% (w/w) of dry matter.

When in the acid form or in the form of a derivative, they can be used in a concentration of 1 ppm to 10% (w/w) of dry matter, preferably 0.02% to 1% of dry matter.

As regards skin re-structuring, repair and protection, it may be of interest to associate in a formulation the purified lactone fraction, which may or may not already have been mixed with the sophorolipids as mentioned above, with ascorbic acid for its dermal re-structuring properties, with vitamin E and its esters, for its active role in anti-radical protection, and/or with vitamin A and its esters, in particular retinyl palmitate, to improve repair of the connective tissue and the epidermis during actinic ageing, inter alia.

It may also be advantageous to combine the purified lactone fraction which may or may not be mixed with other sophorolipids, with alpha or beta hydroxyacids containing 2 to 7 carbon atoms (lactic acid, malic acid, tartaric acid, glycolic acid, citric acid, iso-citric acid, salicylic acid . . . ) which may or may not be in the form of their salts, and their esters, the beneficial role of which has been extensively described in connection with epidermis renewal.

The invention will be better understood from the following Examples:

EXAMPLE 1

Preparation of a Lactone Fraction

| Dry matter | $^2$30% ± 2% |
|---|---|
| pH | 7 ± 0.5 |
| Minerals | $^2$2% |
| Free sugars | $^2$1% |
| Free fatty acids | $^2$3% |
| Ash | $^2$0.04% |
| Density | 1.03 at 20° C. |
| Viscosity | 115.3 mPa.s at 20° C. |
| | 62.4 mPa.s at 40° C. |

They were vacuum dried at 110° C. and taken up in hot ethanol. They were then crystallised at plus 6° C. for 16 hours and filtered.

The crystals obtained were dissolved in ethanol and the solution was re-crystallised at +6° C. for 16 hours. After filtering, the lactone fraction obtained was washed and dried. The white solid obtained comprised 95% by weight of lactones with the following distribution:

| Diacetylated lactones | 87.8% |
|---|---|
| Monoacetylated lactones | 5.3% |
| Non acetylated lactones | 1.9% |

The powdered product was used in an aqueous 50 mg/l solution, pH 5±0.5, to carry out the tests.

Cutaneous and Ocular Tolerance

Cutaneous Tolerance

The local tolerance of the purified product was studied using human skin explants. It was evaluated by histological examination of the effects of the product on the epidermal morphology.

The explants were incubated for 18 h at 37° C. in an atmosphere containing 5% of $CO_2$ in the presence of the purified sophorolipid fraction. Histological observations on the explants under these conditions did not show any morphological alteration. The tested product could thus be considered to be a non irritant.

Occular Tolerance

The ocular tolerance of the product was evaluated it vitro using the PREDISAFE method.

This method has been shown to have a high level of correlation with the Draize test and a high level of reproducibility.

The toxicity score for purified lactone sophorolipids was less than 15 on an arbitrary scale of ocular tolerance graduated from 0 to 50.

The predictive classification of the product as regards ocular tolerance, placed the product in class I. a weak irritant.

EXAMPLE 2

Comparative Effects of Unrefined Sophorolipids and of the Purified Lactone Fraction of Sophorolipids on Collagen Neosynthesis in Normal Human Dermal Fibroblast Cultures The effect of purified lactones on the synthesis of collagens in normal human dermal fibroblast cultures was studied. Collagyens are quantitatively the major dermal proteins. Proline and hydroxyproline constitute 30% of the constituent amino acids of collagens (a high percentage and much higher than that of the majority of other fibroblast proteins). Hydroxyproline is not an amino acid incorporated during the synthesis of collagens, as is the case with proline. Hydroxylation of proline, which leads to the presence of hydroxyproline in collagens, is a collagen maturation process which occurs once synthesis is complete. Measuring the incorporation of tritiated proline into fibroblast proteins thus provides a good index of collagen neosynthesis. Finally, to improve the specificity of this index, the high molecular weight proteins, which almost exclusively correspond to collagens, were separated by ultrafiltration.

Collagen neosynthesis was measured by monitoring the incorporation of radiolabelled proline into newly synthesised fibroblast proteins. These fibroblast proteins are present (1) in cells, (2) in the matrix, deposited in the culture support (under the cells) and (3) in the culture medium, in the form of secreted proteins. Fractions (1) and (2) were measured together and grouped under the title "cell layer collagens". Fraction (3) was designated "secreted collagens".

The effects of the product on cell division were evaluated by measuring the DNA and proteins in the cell layers after 3 days of incubation.

The effects of the purified sophorolipid fraction were compared with those observed in the presence of an initial mixture of unrefined sophorolipids and ascorbic acid used as a reference product.

Protocol

Test Systems

Fibroblasts were isolated from the operative residue of abdominal plastic surgery carried out on a 19 year old female. The cells were cultivated in fibroblast culture medium (FCM) at 37° C. in a moist atmosphere containing 5% of $CO_2$ until confluence of the monolayers.

The culture medium used was fibroblast culture medium (FCM), constituted by MEM/M199 (¾, ¼, v/v) with added penicillin (50 IU/ml), streptomycin (50 µg/ml), sodium bicarbonate (0.2%, wv/v) and SVF (10%, v/v).

Product Dilition and Incubation with Test System

The fibroblast incubation medium (FIM) with the products was constituted by MEM/M199 (¾, ¼, v/v) with added penicillin (50 IU/ml), streptomycin (50 µg/ml), sodium bicarbonate (0.2%, w/v) and SVF (2%, v/v). It contained 1 µCi/ml of tritiated proline.

The purified lactone fraction was diluted in FIM and was tested at 0.02, 0.08 and 0.4 µg/ml (dry matter).

The unrefined sophorolipids were tested at 0.08; 0.4 and 2 µg/ml.

The ascorbic acid was tested at 100 µg/ml (0.5 mM) in FIM.

The fibroblast cultures were incubated for 3 days at 37° C. in a moist atmosphere containing 5% of $CO_2$.

Reference cultures, incubated in the absence of the products to be tested, were produced in parallel.

The tests were carried out in triplicate.

Measurement of Cell Division

After incubation, the incubation media were removed then the cell layers were rinsed with PBS The cells were then lysed by ultrasound. The DNA was assayed using a fluorimetric method using HOECHST 33258 reactant. The proteins in the cell lysate were assayed using the Coomassie Blue method described by Bradford. These assays ensured a suitable interpretation of the results obtained for collagen neosynthesis.

Collagen Neosynthesis Measurenzents

Measurement of incorporation of tritiated proline into "cell layer collagens" the incorporation of tritiated proline into neosynthesised fibroblast proteins, the proteins present in the cells and deposited in the extracellular matrix, was evaluated after 3 days of incubation. The radioactivity of the cell lysate obtained as described above was measured by liquid scintillation with a β particle counter. The values were expressed in cpm per cell layer.

Measurement of incorporation of tritiated proline into "secreted collagens": the incorporation of tritiated proline into neosynthesised collagens secreted in the culture medium was evaluated after 3 days of incubation. The radioactive precursor and the small proteins were eliminated using Nanosep 30 kD filters. The radioactivity of the high molecular weight protein fraction (retained on the filters) corresponded almost exclusively to the secreted collagens and was measured by liquid scintillation with a β particle counter. The values were expressed in cpm per sample.

Treatment of data: the groups of data (reference group and treated groups) were processed by a one-way variance analysis (ANOVA 1, p<0.05) followed by a Dunnett test (p<0.05). The effect of the products was thus compared with the control group.

Results

After 3 days incubation, the unrefined sophorolipids did not modify the protein content of the cell layer (Table 1). The purified lactone fraction increased neither the quantity of DNA nor the quantity of proteins contained in the cell layers (Tables 1 and 2).

Effect of Products on Neosvnthesis of Collaoens After 3 Days Incubation

After 3 days incubation, 100 µg/ml ascorbic acid increased the "cell layer collagens" by a factor of 0.68 and the "secreted collagens" by a factor of 1.81 (Table 3).

These results were expected and validated this part of the study.

The unrefined sophorolipids at 0.08, 0.4 and 2 µg/ml increased the "cell layer collagens" by a factor of 1.63; 1.50 and 1.44 respectively. At the same concentrations, they increased the "secreted collaens" by a factor of 1.39, 1.29 and 1.18. The purified lactone fraction tested at 0.02, 0.08 and 0.4 µg/ml had no effect on the quantity of collagens contained in the cell layers (Table 3). In contrast, at 0.02; 0.08 and 0.4 µg/ml, it increased the quantity of "secreted collagens" by a factor of 2.12; 2.55 and 1.89 respectively (Table 3).

TABLE 1

Effect of products on the protein content of cell layers after 3 days incubation

| | Sophorolipids, unrefined (µg/ml) | | | Purified lactone fraction (µg/ml) | | | Ascorbic acid |
|---|---|---|---|---|---|---|---|
| | 0.08 | 0.4 | 2 | 0.02 | 0.08 | 0.4 | 100 µg/ml |
| Proteins in cell layer (% of reference) | 92 | 106 | 99 | 88 | 94 | 96 | 108 |

TABLE 2

Effect of purified lactone fraction on DNA content of cultured normal human dermal fibroblasts after 3 days of incubation

| | Ascorbic acid | Purified lactone fraction (µg/ml) | | |
|---|---|---|---|---|
| Reference | 100 µg/ml | 0.02 | 0.08 | 0.4 |
| 7 | 6 | 7 | 8.7 | 7.3 |
| 6 | 6 | 5 | 6.3 | 8 |
| 11 | 10 | 6 | 7 | 8 |
| x = 8.35 | 7.5 | 6 | 7.3 | 7.8 |
| +/− | +/− | +/− | +/− | +/− |
| σ = 3 | 2.5 | 0.3 | 1.2 | 0.23 |
| *100* | *90* | *72* | *87* | *93.5* |

The results are expressed in µg/cell layer
In bold: mean and standard deviation σ
*In italics*: percentage of control.

TABLE 3

Effect of purified lactone fraction, unrefined sophorolipids and ascorbic acid on neosynthesis of "secreted collagens" and "cell layer collagens" after 3 days incubation

|  |  | Unrefined sophorolipids (µg/ml) | | | Purified lactone fraction (µg/ml) | | | Ascorbic acid |
|---|---|---|---|---|---|---|---|---|
|  |  | 0.08 | 0.4 | 2 | 0.02 | 0.08 | 0.4 | 100 µg/ml |
| Cell layer | Collagens % of control | 163%* | 150%* | 144%* | 116% | 97% | 91% | 168%* |
| Culture medium | Secreted collagens, % of control | 139%* | 129% | 118% | 212%* | 255%* | 189%* | 181%* |

*Result significantly different from control group ($p < 0.05$).

The collagens are quantitatively the major proteins of the dermis and play an important role as regards the structure of the dermis and because of this, after synthesis must be secreted into the extracellular matrix. The purified lactone fraction has a stimulating effect on collagen neosynthesis which is higher than that of the unrefined sophorolipid mixture and that of ascorbic acid.

If only the "secreted collagens" in the medium are considered under identical experimental conditions, the purified fraction can increase the secretion of new collagen fibres by a factor of 2.55 compared with the control as against a factor of 1.39 with unrefined sophorolipids and a factor of 1.81 with ascorbic acid.

Its effect occurs more rapidly and appears to stimulate the fibroblast cells more strongly than the unrefined sophorolipid mixture. The purified molecule appears to be more available and more active in low doses than the initial mixture.

EXAMPLE 3

Formulation

The purified sophorolipid fraction in its lactone form can be used in cosmetically and/or dermatologically acceptable media, i.e., media which are compatible with the skin, the mucous membranes, the hair and the scalp.

It can be incorporated into all galenical forms which are appropriate for topical application and in particular in the form of emulsions obtained by dispersion of an oily phase in an aqueous phase (O/W) or the converse (W/O), a silicone/water emulsion, or an emulsion with a lamellar structure.

For preparations of aqueous, hydroalcoholic or oily solutions or aqueous, hydroalcoholic or oily gels, or serums, or lotions, it may be appropriate to dissolve the purified lactone fraction in a suitable solvent or in a mixture of unrefined sophorolipids.

The purified lactone sophorolipid product is of importance in the formulation of dermis anti-ageing, repair and re-structuring products because of its effect on the stimulation of dermis cells. By encouraging the synthesis of new collagen fibres, purified lactone sophorolipids can be used both as a preventative measure against ageing of the skin and it can be used in creams for treating or caring for the face, hands, feet and body, and in body milks, lotions and gels for the skin.

|  | % |
|---|---|
| 1. Oil/water Type Cream |  |
| Tefose 2561 | 18.00 |
| Isostearyl isostearate | 6.0 |
| Glyceryl stearate | 1.00 |
| Fondix G | 2.00 |
| Purified lactone fraction of sophorolipids | 0.100 |
| Water, qsp | 100 |

| Tefose 2561 | PEG-6 stearate/Ceteth-20/glyceryl stearate/steareth-20 |
|---|---|
| Cetiol V | Decyl oleate |
| Fondix G | Propylene glycol/sodium methylparaben/sodium dehydroacetate/sorbic acid/tetrasodium EDTA |

|  | % |
|---|---|
| 2. Water/silicone type cream |  |
| SPG 128 VP | 10.00 |
| Cyclomethicone | 10.00 |
| Beeswax | 3.00 |
| Polyglycerol-3-stearate | 2.00 |
| NaCl | 2.00 |
| Liquapar oil | 0.40 |
| Purified lactone fraction of sophorolipids | 0.10 |
| Water qsp | 100 |
| 3. Water/oil type cream |  |
| Plurol | 5.00 |
| Mineral oil | 19.00 |
| NaCl | 1.00 |
| $MgSO_4$ | 1.00 |
| Liquapar oil | 0.30 |
| Purified lactone fraction of sophorolipids | 0.10 |
| Water qsp | 100 |
| 4. Cream with lamellar structure |  |
| Methylglucosesesquistearate/sorbitan stearate | 5.00 |
| Stearine | 4.00 |
| Cetearyl alcohol | 1.80 |
| Octyldodecanol | 9.00 |
| Capric/caprylic triglycerides | 11.00 |
| Isopropyl myristate | 6.00 |
| Glycerol | 3.00 |
| Purified lactone fraction of sophorolipids | 0.100 |
| Water qsp | 100 |

The oily phase was melted, and the aqueous phase was added with vigorous stirring (>3000 rpm) and then cooled.

| | % |
|---|---|
| 5. Cream with lamellar structure | |
| Methylglucosesesquistearate/sorbitan stearate | 5.00 |
| Stearine | 4.00 |
| Cetearyl alcohol | 1.80 |
| Octyldodecanol | 9.00 |
| Capric/caprylic triglycerides | 11.00 |
| Isopropyl myristate | 6.00 |
| Glycerol | 3.00 |
| Sepigel 305 | 0.20 |
| Purified lactone fraction of sophorolipids | 0.100 |
| Unrefined sophorolipids | 1.00 |
| Water qsp | 100 |

Sépigel 305: Polyacrylamide/C13–14 isoparaffin/laureth-7

| | % |
|---|---|
| 5. Xanthane based gel | |
| Xanthane | 0.40 |
| Purified lactone fraction of sophorolipids | 0.10 |
| Unrefined sophorolipids | 1.00 |
| Water qsp | 100 |

What is claimed is:

1. A method for stimulating the metabolism of skin dermis fibroblasts which comprises topically applying a composition comprising sophorolipids, wherein at least about 95% by weight of the sophorolipids in the composition are in the lactone form and a major portion of said sophorolipids in the lactone form are diacetylated lactones.

2. The method of claim 1, wherein the composition comprising sophorolipids is further effective for stimulating collagen neosynthesis.

3. The method of claim 1, wherein 70% by weight of the sophorolipids in lactone form are diacetylated lactones.

4. The method of claim 1, wherein 80% by weight of the sophorolipids in lactone form are diacetylated lactones.

5. The method of claim 1, wherein the composition contains said sophorolipids in a concentration of from 0.01 ppm to 5% (w/w) of dry matter in the composition.

6. The method of claim 1, in which said sophorolipids are contained in a water/oil or oil/water type emulsion, a gel, a serum, a lotion or a shampoo.

7. The method of claim 1, wherein the composition comprises 5% by weight or less of unrefined sophorolipids, sophorolipids in the deacetylated acid form, or acid sophorolipids, the acid function of which is at least partially in the form of an ester.

8. The method of claim 1, wherein the composition further comprises at least one product selected from the group consisting of ascorbic acid, vitamin E and its esters, vitamin A and its esters and alpha or beta hydroxy acids containing 2 to 7 carbon atoms and esters thereof.

9. The method of claim 5, wherein the concentration is from 50 ppm to 1% of dry matter.

10. The method of claim 6, wherein 80% by weight of the sophorolipids in lactone form are diacetylated lactones.

11. The method of claim 7, wherein 80% by weight of the sophorolipids in lactone form are diacetylated lactones.

12. A composition according to claim 8, wherein 80% by weight of the sophorolipids in lactone form are diacetylated lactones.

* * * * *